United States Patent [19]

Faure et al.

[11] Patent Number: 4,774,378
[45] Date of Patent: Sep. 27, 1988

[54] PROCESS FOR PRODUCTION OF STYRENE

[75] Inventors: Jacques Faure, Verneuil En Halatte; Philippe Gillet, Saint Avold; Raymond Hess, Forbach; Jean-Marc Pognon, Teting Sur Nied, all of France

[73] Assignee: Norsolor, Paris La Defense, France

[21] Appl. No.: 29,105

[22] Filed: Mar. 23, 1987

[30] Foreign Application Priority Data

Mar. 21, 1986 [FR] France ............................... 86 04066

[51] Int. Cl.$^4$ .............................................. C07C 4/02
[52] U.S. Cl. .................................................. 585/441
[58] Field of Search ....................................... 585/441

[56] References Cited

U.S. PATENT DOCUMENTS 3,660,510  5/1972  Kindler et al. ...................... 585/441
4,113,787  9/1978  Ward .................................. 585/441
4,347,396  8/1982  Takano et al. ...................... 585/441

Primary Examiner—Curtis R. Davis
Attorney, Agent, or Firm—Millen & White

[57] ABSTRACT

The present invention relates to a process for the production of styrene by the catalytic dehydrogenation of ethylbenzene into styrene in the presence of steam which is, in a first stage, used for heating the reaction effluents, and then used as diluent for ethylbenzene. This process is characterized in that:

a molar ratio of steam:ethylbenzene of between 5 and 13 is used, the temperature in the dehydrogenation reactors is between 580° and 645° C., the average pressure in the first reactor is 0.6–1 kg/cm$^2$ and those in the second and the third reactors is 0.4–0.7 kg/cm$^2$, and the hourly space velocity of liquid ethylbenzene is 0.20–0.35 h$^{-1}$.

12 Claims, 1 Drawing Sheet

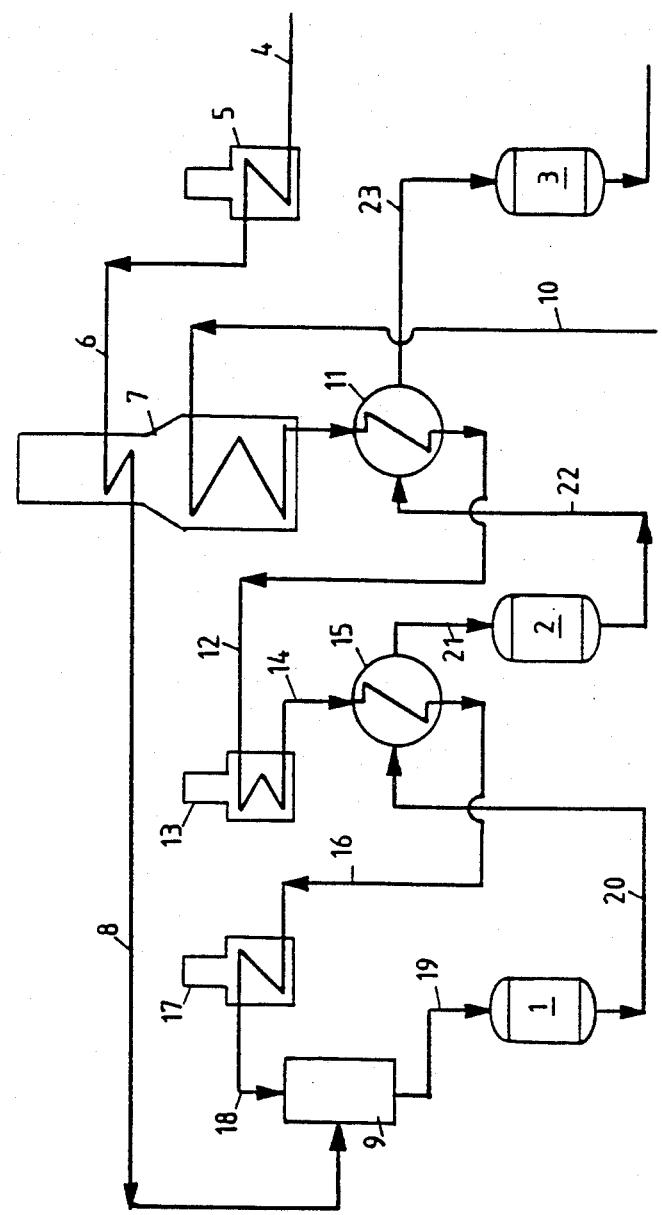
- FIGURE 1 -

PROCESS FOR PRODUCTION OF STYRENE

BACKGROUND OF THE INVENTION

The present invention relates to a new process for producing styrene by the catalytic dehydrogenation of ethylbenzene into styrene in the presence of steam.

Styrene is widely used as raw material for the production of a large number of resins, plastics and elastomers, the extent of its use being mainly attributed to the suitability of styrene to be easily polymerized, for example, into polystyrene, or to be copolymerized, for example with butadiene, to produce rubbers.

The production of styrene, as regards the dehydrogenation process as well as the variety of catalysts used in this process, is well known. As present, the main research objective lies in the improvement of the profitability of the process. Especially, a process for the dehydrogenation of ethylbenzene according to which the dehydrogenation is carried out in a plant which comprises at least three dehydrogenation reactors in series, and intermediate heating devices for the reactors in which the reaction effluents are subjected to a heating by heat exchange with stream is known. According to this process, steam is first of all used for heating the reaction effluents and it is then mixed with ethylbenzene at the inlet of the first reactor. The operating conditions adopted in this process are the mixing of 3 to 10 moles of steam with 1 mole of ethylbenzene, and a temperature and a pressure at the inlet of the last reactor of 600°–680° C. and 0.4–0.8 kg/cm$^2$, respectively. The temperature and pressure conditions at the inlet of the other reactors are 600°–680° C. and 2–0.4 kg/cm$^2$ (absolute), respectively, and the overall space velocity of ethylbenzene is equal to or greater than 0.44 h$^{-1}$. By hourly space velocity of ethylbenzene is meant the ratio of the volume flowrate of ethylbenzene to the total volume of the catalyst. According to this process, an ethylbenzene conversion rate of the order of 65–75%, or even greater, and a molar selectivity of the order of 90% are obtained. However, the implementation of such a process, over a period of time, leads to a deterioration in the styrene selectivity as well as in the ethylbenzene conversion rate which may, nevertheless, be limited by increasing the reaction temperatures. In fact, gradual degradation of the catalyst and appearance of carbon deposits on this catalyst are observed over a period of time. Additionally, the presence of hot points along the production line (especially in the intermediate heating devices) gives rise to thermal degradation reactions producing heavy and choking compounds. It is estimated that the rate of heavy products formed is of the order of 17000 ppm, expressed per ton of effluent hydrocarbons, or even greater. In the end, an increase in charge loss, a decrease in the efficiency of the catalyst and, therefore, the need for frequent cleaning, results therefrom. With a view to eliminating the drawbacks of such a process, the Applicant Company has developed a new process for the dehydrogenation of ethylbenzene which makes it possible to obtain excellent ethylbenzene conversion rates, greater than 73%, and a molar selectivity greater than 93%.

SUMMARY OF THE INVENTION

More precisely, the subject of the invention is a process for producing styrene by the catalyst dehydrogenation of ethylbenzene according to which the dehydrogenation is carried out in a plant which comprises three dehydrogenation reactors in series, one or more heating devices arranged between the reactors in which the reaction effluents are subjected to a heating by heat exchange with steam, which is used, in a first stage, to heat the reaction effluents, and which is mixed, in a second stage, with the ethylbenzene at the inlet of the first dehydrogenation reactor. The process according to the invention is characterized in that:

ethylbenzene is mixed with steam in a molar ratio of steam:ethylbenzene of between 5:1 and 13:1, the mixture is heated at the inlet of the said reactors to a temperature of between 580° and 645° C., an average pressure in the first reactor of between 0.6 and 1.0 kg/cm$^2$, expressed as absolute pressure, and a pressure of between 0.40 and 0.70 kg/cm$^2$, expressed as absolute pressure, in the second and the third reactors are maintained, and an overall space velocity of liquid ethylbenzene of between 0.20 and 0.35 h$^{-1}$ is imposed.

According to a preferred embodiment of the process according to the invention an overall space velocity of liquid ethylbenzene of between 0.24 and 0.30 h$^{-1}$ is imposed.

Preferably, the temperature at the inlet of the reactors is maintained between 595° and 630° C.

Preferably still, the average pressure in the first reactor is between 0.6 and 0.8 kg/cm$^2$, expressed as absolute pressure, the average pressure in the second reactor is between 0.5 and 0.7 kg/cm$^2$, expressed as absolute pressure or the average pressure, in the third reactor is between 0.4 and 0.6 kg/cm$^2$, expressed as absolute pressure.

Preferably still, a molar ratio of steam:ethylbenzene of between 7:1 and 13:1 is imposed, the conversion of ethylbenzene and the molar selectivity being higher in this range.

The process according to the invention may be used with conventional catalysts used for the dehydrogenation of ethylbenzene. Catalysts based on iron oxide and, in particular, those which contain potassium, may especially be mentioned.

Any ethylbenzene dehydrogenation reactor may be employed for implementing the process according to the invention. However, radial reactors of the type described in French Patent No. 2,365,370 are preferably used.

In accordance with the process according to the invention, which is carried out under moderate conditions of temperature and at low pressure and low overall space velocity of the liquid ethylbenzene, a significant restriction is achieved in the formation of heavy degradation products. In fact, in accordance with the process according to the invention, the rate of heavy products formed does not exceed 5000 ppm per tonne of effluent hydrocarbons.

In accordance with the process according to the invention, ethylbenzene conversion rates which may reach 75% or higher, and a selectivity of the order of 95% or even greater, are obtained.

Moreover, the decrease in the formation of heavy and choking degradation products enables this performance to be maintained over a period of time and avoids the frequent stoppages of the plants for cleaning.

BRIEF DESCRIPTION OF THE DRAWINGS

The invention will be better understood on reading the practical embodiments of the present invention, given by way of indication and without implied limitation, and carried out using the styrene manufacturing plant described below and shown in FIG. 1.

According to the invention, the plant shown in FIG. 1 comprises three dehydrogenation reactors 1, 2 and 3, arranged in series.

DETAILED DESCRIPTION OF THE DRAWINGS

Ethylbenzene is first of all vaporized in an exchanger (not shown in FIG. 1) and then introduced through the circuit 4 into a furnace 5 and then through the circuit 6 into the furnace 7. The ethylbenzene is then brought through the circuit 8 into the mixer 9 to be mixed therein with steam.

Water, which has previously been vapourized in a boiler (not shown in FIG. 1), is brought through the circuit 10 into the furnace 7. The steam then undergoes a series of heat exchanges, thus playing the role of a high-temperature heat exchange fluid:

- at the outlet of the furnace 7, the steam is brought into the indirect heat exchanger 11 to heat the effluents originating from the reactor 2,
- the steam is then brought through the circuit 12 into the furnace 13 to be heated therein,
- the steam is then introduced through the circuit 14 into the indirect heat exchanger 15 to heat the effluents from the reactor 1,
- the steam is then introduced through the circuit 16 into the furnace 17 to be reheated therein, and the steam is then injected through the circuit 18 into the mixer 9 to be mixed with ethylbenzene therein.

As it leaves the mixer 9, the ethylbenzene-steam reaction mixture, the steam:ethylbenzene molar ratio of which is, according to the invention, between 5 and 13, has a temperature of the order of 580°–645° C.

The reaction mixture thus obtained is injected through the circuit 19 into the reactor 1 in which it passes through the first catalytic bed. The pressure at the boundaries of this reactor must be adjusted so as to have an average pressure, expressed as absolute pressure, of 0.6–1 kg/cm$^2$ and preferably of 0.6 to 0.8 kg/cm$^2$. On exit from the reactor 1, the reaction mixture or effluent is directed through the circuit 20 into the heat exchanger 15 for heating. Because of the endothermic nature of the dehydrogenation reaction, the mixture undergoes a temperature drop of a few tens of degrees in the dehydrogenation reactors 1, 2 and 3. Advantageously and in accordance with the invention, the reaction effluents are heated in the heat exchangers 15 and 11 before being injected into the reactors 2 and 3 respectively. On exit from the exchanger 15, the reaction mixture has a temperature sufficient to undergo a dehydrogenation once again, at a temperature of between 580° and 645° C. The effluent is therefore directed through the circuit 21 into the reactor 2 in which it passes through the second catalytic bed. The pressure at the boundaries of this reactor must be adjusted so as to have an average pressure, expressed as absolute pressure, preferably of 0.5–0.7 kg/cm$^2$, and preferably still, of 0.52–0.65 kg/cm$^2$. On exit from this reactor, the effluent is brought through the circuit 22 into the heat exchanger 11 for heating and then through the circuit 23 into the reactor 3 in which it passes through the third catalytic bed. The pressure at the boundaries of this reactor must be adjusted so as to have an average pressure, expressed as absolute pressure, preferably of 0.4–0.6 kg/cm$^2$, and preferably still, of 0.4–0.5 kg/cm$^2$.

On exit from the reaction zone, the effluent is first of all directed into devices for energy recovery (not shown in FIG. 1) and is then directed towards the styrene purification phase.

The space velocity of liquid ethylbenzene in the reactors 1, 2 and 3 is adjusted so as to have an overall space velocity of between 0.20 and 0.35 h$^{-1}$ and preferably between 0.24 and 0.30 h$^{-1}$.

EXAMPLES

Examples of practical implementation Nos. 1, 2, 3, 4 and 5 and comparative examples 6 and 7.

The catalytic dehydrogenation of the ethylbenzene-steam mixture was carried out using a plant, the block diagram for the production of which is shown in FIG. 1. The reaction conditions for the dehydrogenation and the results are given in table I. Example Nos. 1, 2, 3, 4 and 5 relate to the implementation of the dehydrogenation process according to the invention whereas the comparative examples 6 and 7 correspond to the implementation of the conventional dehydrogenation process, the operating conditions of which are mentioned in the first part of our application.

In addition, the catalyst used in the examples is based on iron oxide and contains especially potassium.

TABLE No. 1

|  | EXAMPLES | | | | | COMPARATIVE EXAMPLES | |
|---|---|---|---|---|---|---|---|
|  | N° 1 | N° 2 | N° 3 | N° 4 | N° 5 | N° 6 | N° 7 |
| Molar ratio of steam:ethylbenzene | 12.4 | 9.4 | 8.20 | 7 | 5.3 | 6 | 4 |
| Temp. (in °C.) at the inlet of the | | | | | | | |
| 1st reactor | 620 | 625 | 620 | 595 | 600 | 650 | 650 |
| 2nd reactor | 620 | 625 | 620 | 600 | 600 | 650 | 650 |
| 3rd reactor | 620 | 625 | 620 | 600 | 600 | 650 | 650 |
| Overall space velocity (in h$^{-1}$) | 0.24 | 0.27 | 0.30 | 0.25 | 0.27 | 0.44 | 0.44 |
| Average pressure (in kg/cm$^2$) | | | | | | | |
| 1st reactor | 0.84 | 0.76 | 0.75 | 0.72 | 0.71 | 0.90 | 0.86 |
| 2nd reactor | 0.64 | 0.60 | 0.58 | 0.59 | 0.57 | 0.81 | 0.80 |
| 3rd reactor | 0.50 | 0.47 | 0.45 | 0.47 | 0.47 | 0.68 | 0.68 |
| Conversion of ethylbenzene | 80 | 73 | 73.3 | 64.7 | 56.6 | 72.1 | 66.7 |
| Selectivity (in mole %) | 95.8 | 94.9 | 93.6 | 93.4 | 94.5 | 90.9 | 89.8 |
| Heavies formed (in ppm) | 1200 | 2400 | 4000 | 900–1000 | 2000 | 16800 | 18000 |

We claim:

1. A process for producing styrene by catalytic dehydrogenation of ethylbenzene wherein the dehydrogenation is conducted in three separate dehydrogenation zones in series, one or more heating means arranged between said zones wherein reaction effluents are heated by indirect heat exchange with steam which after being used to heat said reaction effluents, is mixed with the ethylbenzene at the inlet of the first dehydrogenation reaction zone and wherein:

the ethylbenzene is mixed with the steam in a molar ratio, steam: ethylbenzene, of between 5:1 and 13:1, the resultant mixture is heated at the inlet of the reaction zones to a temperature of between 580° and 645° C., an average pressure in the first reaction zone of between 0.6 and 1 kg/cm$^2$, expressed as absolute pressure, and a pressure of between 0.40 and 0.70 kg/cm$^2$, expressed as absolute pressure, in the second an the third reaction zones are maintained, and an overall space velocity of the liquid ethylbenzene therein of between 0.20 and 0.35 h$^{-1}$ is imposed.

2. Process according to claim 1, wherein the overall space velocity of the liquid ethylbenzene is between 0.24 and 0.30 h$^{-1}$.

3. Process according to claim 1 or 2, wherein the temperature at the inlet of the reactors is maintained between 595° and 630° C.

4. Process according to claim 1, wherein the average pressure in the first reaction zone is between 0.6 and 0.8 kg/cm$^2$, expressed as absolute pressure.

5. Process according to claim 1, wherein the average pressure in the second reaction zone is between 0.5 and 0.7 kg/cm$^2$, expressed as absolute pressure.

6. Process according to claim 1, wherein the average pressure in the second reaction zone is between 0.52 and 0.65 kg/cm$^2$, expressed as absolute pressure.

7. Process according to claim 1, wherein the average pressure in the third reaction zone is between 0.4 and 0.6 kg/cm$^2$, expressed as absolute pressure.

8. Process according to claim 1, wherein the average pressure in the third reaction zone is between 0.4 and 0.5 kg/cm$^2$, expressed as absolute pressure.

9. Process according to claim 1, wherein the overall space velocity of the liquid ethylbenzene is between 0.24 and 0.30 h$^{-1}$, wherein the temperature at the inlet of the reaction zone is maintained between 595° and 630° C., wherein the average pressure in the first reaction zone is between 0.6 and 0.8 kg/cm$^2$, wherein the average pressure in the second reaction zone is between 0.5 and 0.7 kg/cm$^2$, and wherein the average pressure in the third reaction zone is between 0.4 and 0.6 kg/cm$^2$, expressed as absolute pressure.

10. A process according to claim 1, wherein the steam:ethylbenzene molar ratio is between 7:1 and 13:1.

11. A process according to claim 9, wherein the steam:ethylbenzene molar ratio is between 7:1 and 13:1.

12. A process according to claim 1, wherein the rate of heavy products formed does not exceed 5000 ppm per ton of effluent hydrocarbon

* * * * *